(12) United States Patent
Kadowaki et al.

(10) Patent No.: US 6,193,415 B1
(45) Date of Patent: Feb. 27, 2001

(54) MOBILE DEVICE FOR X-RAY APPARATUS

(75) Inventors: Toshio Kadowaki; Goroh Hirata, both of Kyoto; Toshiaki Nakamura, Shiga; Masahiro Kawano, Osaka, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/357,211

(22) Filed: Jul. 20, 1999

(30) Foreign Application Priority Data

Jul. 31, 1998 (JP) .................................................. 10-218181

(51) Int. Cl.[7] ....................................................... H05G 1/02
(52) U.S. Cl. ............................................. 378/198; 378/197
(58) Field of Search ..................................... 378/198, 197

(56) References Cited

U.S. PATENT DOCUMENTS 2,041,242 * 5/1936 Goldfield ............................. 378/198

* cited by examiner

*Primary Examiner*—Craig E. Church
(74) *Attorney, Agent, or Firm*—Kanesaka & Takeuchi

(57) ABSTRACT

A mobile device for an X-ray apparatus is formed of a freely rotatable hollow column disposed on a mobile base, a holding section for holding an X-ray tube in a vertical direction along the column, and a counter weight connected through a wire to the holding section to be suspended inside the column. A column rotating section formed of a bearing portion and a rotational shaft with a hollow part is disposed in the mobile base. A lower part of the counter weight is provided with a convex portion which enters into the hollow part of the rotational shaft. When the holding section for the X-ray tube is elevated to the highest point, the counter weight is lowered to the lowest point, wherein the convex portion of the counter weight enters into the hollow part of the rotational shaft. Thus, a volume of the hollow part can be utilized as a part of the volume of the counter weight to allow the counter weight to be made of iron and the like, other than lead.

7 Claims, 2 Drawing Sheets

MOBILE DEVICE FOR X-RAY APPARATUS

BACKGROUND OF THE INVENTION AND RELATED ART STATEMENT

The present invention relates to a mobile device for an X-ray apparatus, and more particularly, the invention relates to an X-ray apparatus useful for a circuit examination by a doctor, wherein an X-ray tube holding section moves vertically or up and down along a rotatable column disposed on a base or truck.

A mobile type X-ray apparatus for a circuit examination by a. doctor in a conventional cordless condenser type is shown in FIG. 2. In the mobile type X-ray apparatus, a controller 13 is placed on a mobile base or truck 1, and a column 3 for suspending and holding an X-ray tube 10 is disposed upright or vertically.

The controller 13 placed on the mobile truck 1 is provided with a high-voltage transformer and a condenser or capacitor. A control circuit of the controller 13 is systemized, and an automatically programmed one-touch system is frequently used for photographing operation. It is important for the mobile type X-ray apparatus for a circuit examination by a doctor to be small and light-weight, so that the mobile type X-ray apparatus is moved to a bedroom, a technician room, an operation room, a children room, an X-ray room, an infant room, or the like in a hospital so as to take an X-ray photographing easily at these sites.

The X-ray tube 10 in the mobile type X-ray apparatus can be positioned at any places as an advantage of a mobile type. Namely, the column 3 is freely rotatable as described later, and the X-ray tube 10 is held by the column 3 to be freely movable in a vertical direction. More specifically, the X-ray tube 10 is held at a distal end of a side arm 11 disposed at a carriage 7 attached perpendicularly thereto, and the carriage 7 ascends and descends along the column 3. The X-ray tube 10 can be rotated at the distal end of the side arm 11 in a direction perpendicularly to an axial direction of the tube.

Namely, the hollow column 3 is vertically disposed at a rotational shaft or shaft portion 4 held by a bearing portion 2 provided on the mobile truck 1. On the other hand, the carriage 7 and the side arm 11 ascend and descend along the hollow column 3. A counter weight 8 is hung from one end of a wire 9 to be movable up and down. A pulley 6 is provided at an upper portion of the hollow column 3, and the other end of the wire 9 extending through the pulley 6 is connected to the carriage 7. The weight of the counter weight 8 and weight of the X-ray tube 10 with a holding section therefor, i.e. the carriage 7 and the side arm 11, are set to be the same so as to be balanced. Further, the side arm 11 can be retracted and extended to move the X-ray tube in the front and rear directions.

As described above, the arm portion, i.e. side arm 11, which includes a supporting system and a rotating system for the X-ray tube 10 and is extended and retracted in the horizontal direction, is designed to have a mechanism which allows the side arm 11 to vertically move along the column 3 smoothly with a balanced condition. Also, the side arm 11 or the arm portion is designed so that a collimator, i.e. X-ray emission port, of the X-ray tube 10 can face a part to be photographed of an examinee, i.e. patient, in any directions and in any spatial positions.

Rubber tires are attached to the mobile truck 1, and the mobile truck 1 is designed such that it can freely move into and out of a patient's room, an operation room and an elevator.

Further, the mobile truck 1 includes a braking system, a cassette box, and accessory devices.

The conventional mobile type X-ray apparatus is structured as described above. However, in order to move the X-ray tube 10 up and down smoothly along the column 3 while being well-balanced, the counter weight 8 corresponding to the weight of the X-ray tube 10 is stored in a hollow portion of the column 3, so as to prevent collision with other members which are hung outside the column 3. Since it is necessary for the counter weight 8 to be disposed in a limited inner space of the column 3, the counter weight is required to have a small volume and large specific gravity. Thus, lead is generally used for the counter weight, but it is not preferable to use lead from an environmental viewpoint. When the counter weight 8 is made of iron, in order to hold the large volume of iron corresponding to the volume of the counter weight, it is necessary to make the column 3 thicker or higher. Also, if the thickness and the height of the column are maintained as in the conventional one, there is a problem that the counter weight 8 is extended longer, so that a stroke of the up-and-down movement of the X-ray tube 10 becomes shorter for the length of an extended portion of the counter weight 8.

The present invention has been made in view of the aforementioned problems, and an object of the present invention is to provide a mobile device for an X-ray apparatus, which can be made compact without changing the substantial portion of the apparatus.

Another object of the invention is to provide a mobile device for an X-ray apparatus as stated above, wherein a counter weight for the apparatus can be made of a material suitable for an environment.

Further objects and advantages of the invention will be apparent from the following description of the invention.

SUMMARY OF THE INVENTION

To achieve the above objects, the present invention provides a mobile device for an X-ray apparatus, which includes a mobile base having a bearing portion, a rotational shaft disposed in the bearing portion and having a hollow part, a hollow column fixed to the rotational shaft to be vertically disposed on the mobile base and having a hollow section communicating with the hollow part, and a holding section for an X-ray tube to be movable in a vertical direction along the hollow column. A connecting member or wire is provided in the hollow section of the hollow column to extend downwardly through an upper part of the hollow column. The connecting member has one end connected to the holding section, and a counter weight is connected to the other end of the connecting member to be suspended by the connecting member. The counter weight is situated inside the hollow column to be vertically movable in the hollow column and the hollow part. The counter weight includes a lower part capable of entering into the hollow part of the rotational shaft. Thus, the counter weight is movable throughout an entire length of the hollow section and the hollow part.

In the invention, since the lower part of the counter weight can enter into the hollow part of the rotational shaft, a large space is utilized for moving the counter weight. Thus, the counter weight may be made of iron or the like, and the X-ray tube can be moved up and down smoothly without changing the thickness and the height of the column as compared with the conventional apparatus.

The hollow column and the rotational shaft may be integrally formed together, or formed separately and connected together. The hollow part of the rotational shaft penetrates entirely through the rotational shaft.

An X-ray tube is attached to the holding section for moving the X-ray tube vertically along the hollow column. The holding section includes a carriage attached to the hollow column and a side arm attached to the carriage. The side arm is disposed perpendicularly to the hollow column and holds the X-ray tube at one end thereof.

DETAILED DESCRIPTION OF PREFERRED EMBODIMENTS

Figure 1:
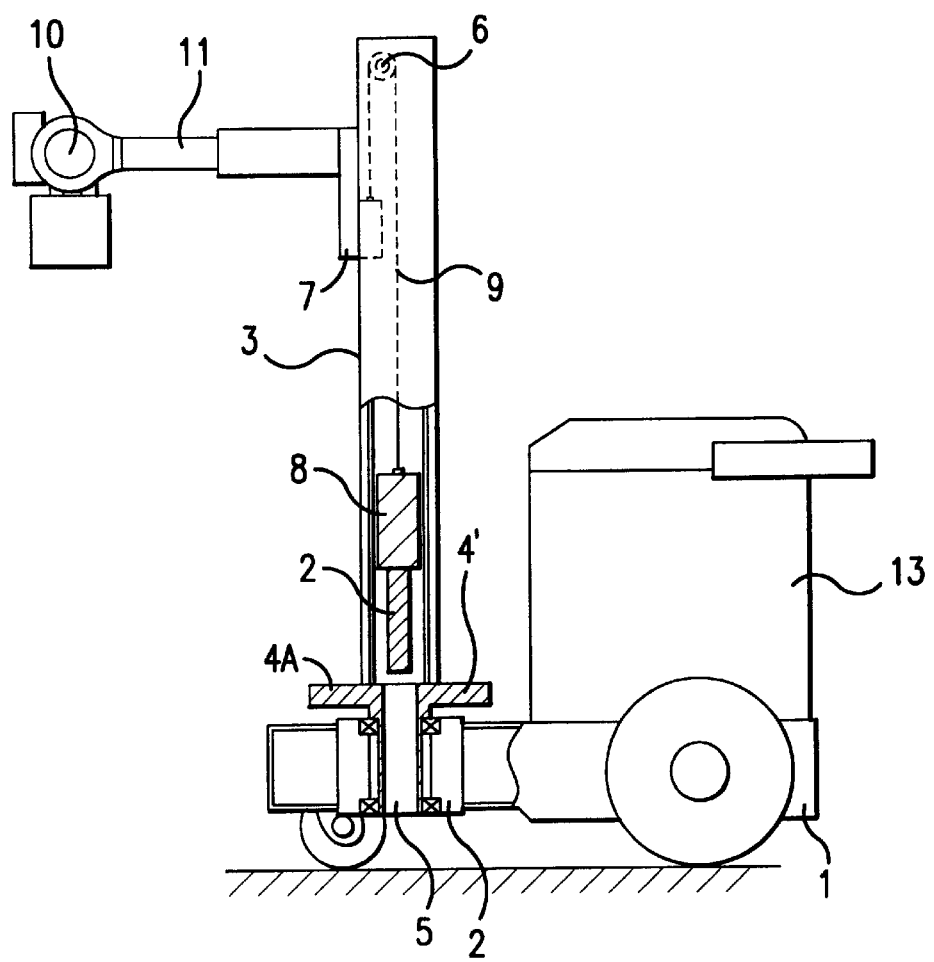
FIG. 1 is an explanatory view showing an embodiment of a mobile device for an X-ray apparatus of the invention.

Hereunder, an embodiment of a mobile device for an X-ray apparatus of the invention will be explained with reference to FIG. 1.

In the apparatus, a controller 13 as an X-ray controlling and generating section, which includes a battery, an inverter, a transformer and a condenser, is placed on a mobile base or truck 1, and a rotatable hollow column 3, which suspends and holds an X-ray tube 10 provided with a collimator, is vertically disposed on the truck 1. In an inner side of the hollow column 3, a counter weight 8 suspended by a wire 9 to be able to move up and down is suspended, and is balanced in weight with the X-ray tube 10 and a holding section therefor. These structures are the same as in the conventional apparatus.

In the above structures, the present invention has the following features. Namely, a bearing portion 2 is provided in the mobile truck 1 as in the conventional apparatus, and a rotational shaft or shaft portion 4A with a flange 4' is attached to the mobile truck 1, but a hollow portion 5 is provided in the rotational shaft 4A. On the other hand, a convex portion 12 according to the invention is formed at a lower part of the counter weight 8. A shape of the convex portion 12 is designed to be able to enter into the hollow portion 5 of the rotational shaft 4A.

A pulley 6 is provided at an upper part of the column 3 as in the conventional apparatus, and a carriage 7 vertically movable along the column 3 by a guiding mechanism (not shown) is connected to the counter weight 8, which is vertically movable inside the column 3, with the convex portion 12 through the wire 9. A side arm 11 for supporting the X-ray tube 10 is fixed to the carriage 7, and the carriage 7, the X-ray tube 10 and the side arm 11 are balanced with the counter weight 8 with the convex portion 12. When the X-ray tube 10 is elevated to the highest point, the counter weight 8 with the convex portion 12 thereof is lowered to the lowest point, so that the convex portion 12 at the lower part of the counter weight 8 enters into the hollow portion 5 of the rotational shaft 4A.

When the X-ray tube is moved up and down, the volume occupied by moving the counter weight is a total volume of the inside of the column and the hollow portion 5. Accordingly, the volume of the counter weight can be increased by the volume of the convex portion 12 as compared to the conventional apparatus. By utilizing the extra volume of the hollow portion 5, however, even if the counter weight is not made of lead, the counter weight made of iron can provide weight for the counter weight which is required. Also, when the counter weight is made of lead, a cross-sectional area of the column 3 can be reduced to a smaller size, and the height of the column 3 can be lowered.

The explanation has been made for the embodiment, wherein the column rotating section is formed of two members, i.e. the bearing portion 2 and the rotational shaft 4A including the hollow portion 5, but the column rotating section can be formed of one member, such as a rotatable wheel bearing. The column section is fitted with the rotatable wheel bearing such that the convex portion 12 of the weight can enter into a hollow portion of the rotatable wheel bearing, and a gear or the like is provided on an outer periphery of the rotatable wheel bearing so as to utilize the gear for a rotating brake on a horizontal plane of the X-ray tube 10 or for automatic positioning.

Figure 3:
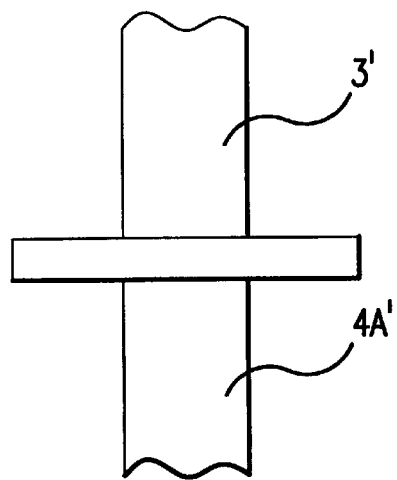
FIG. 3 is an explanatory side view of a column and a rotational shaft integrally formed together.
Figure 2:
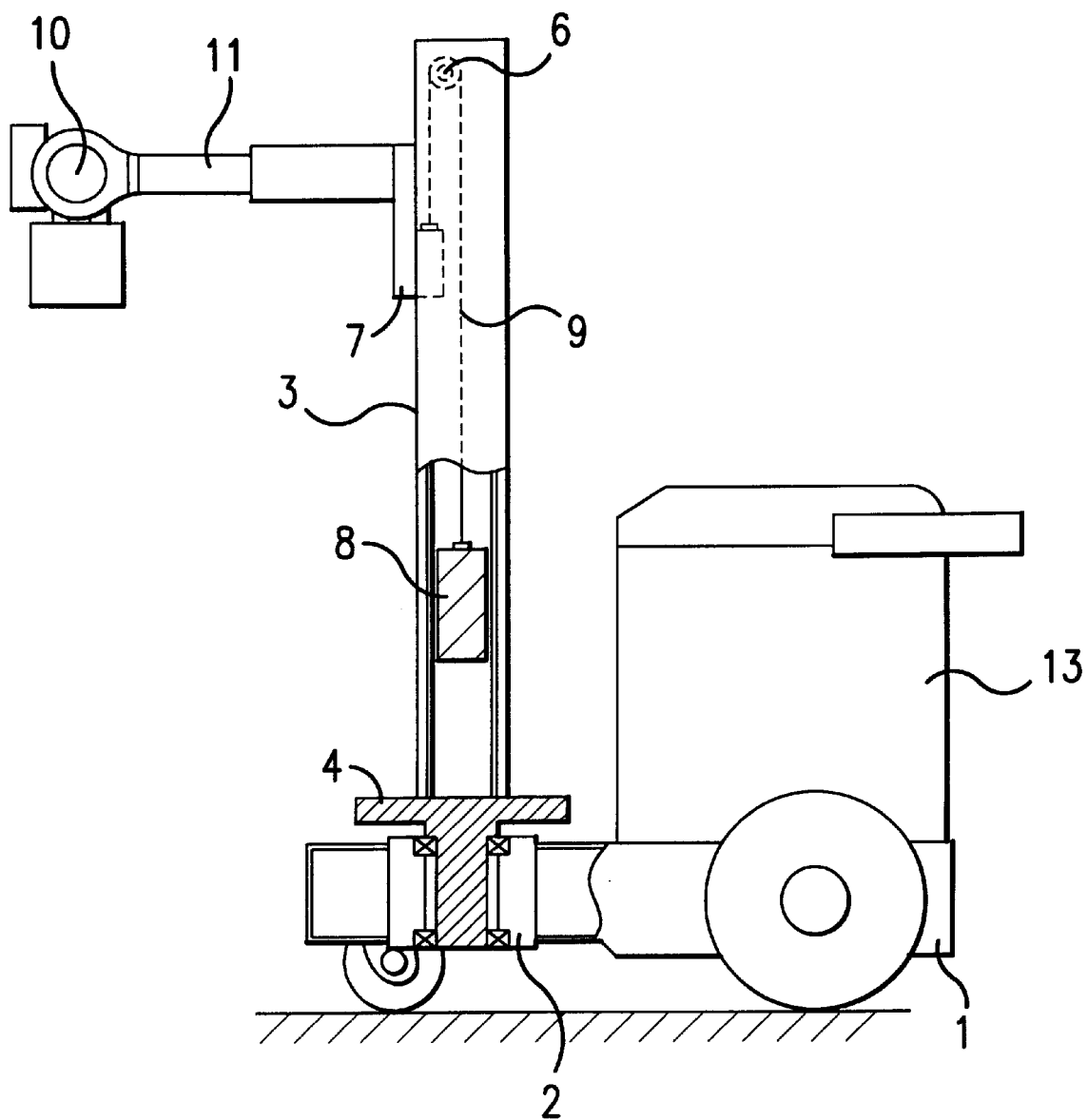
FIG. 2 is an explanatory view showing a convention mobile type X-ray apparatus.

Also, a rotational shaft 4A' can be integrally formed with a column 3', as shown in FIG. 3. Of course, in this case, a portion of the column inserted into the bearing portion 2 functions as the rotation shaft. In this modified example, the diameter of the hollow portion can be the same throughout the entire length thereof, and the convex portion has the same diameter as that of the hollow portion. Namely, the counter weight 8 can be formed as an elongated rod having the uniform diameter throughout the entire length. Even if the rotational shaft is formed separately, the diameter of the hollow portion of the rotational shaft can be the same as that of a hollow part of the column.

In the mobile device for the X-ray apparatus of the invention, when the X-ray tube 10 is moved vertically, the volume occupied by moving the counter weight 8 is a sum of the volume of the inside of the column 3 and the volume of the hollow portion 5 of the rotational shaft. Although the volume of the counter weight 8 is increased by the volume of the convex portion 12 as compared with the conventional apparatus, by utilizing the increase in the volume at the hollow portion 5, the increase of the volume of the convex portion 12 is compensated or offset. Therefore, even if the counter weight is not made of lead resulting in the increase of the volume of the counter weight, the required counter weight can be made, e.g. by iron. Thus, an environmental problem by lead can be avoided. Also, in case the counter weight is made of lead, a cross-sectional area of the column 3 can be reduced to a smaller size, and the height of the column 3 can be lowered.

While the invention has been explained with reference to the specific embodiments of the invention, the explanation is illustrative and the invention is limited only by the appended claims.

What is claimed is:

1. A mobile device for an X-ray apparatus, comprising:

a mobile base having a bearing portion, a rotational shaft disposed in the bearing portion and having a hollow part, a hollow column fixed to the rotational shaft to be vertically disposed on the mobile base and having a hollow section communicating with the hollow part, a holding section for an X-ray tube to be movable in a vertical direction along the hollow column, a connecting member provided in the hollow section of the hollow column to extend downwardly through an upper part of the hollow column, said connecting member having one end connected to the holding section, and a counter weight connected to the other end of the connecting member to be suspended by the connecting member and situated inside the hollow column to be vertically movable in the hollow column and the hollow part, said counter weight including a lower part capable of entering into the hollow part of the rotational shaft so that the counter weight is movable throughout an entire length of the hollow section and the hollow part.

2. A mobile device according to claim 1, wherein said hollow column and the rotational shaft are formed separately and connected together, said rotational shaft having a flange disposed on the mobile base.

3. A mobile device according to claim 2, wherein said hollow part of the rotational shaft penetrates entirely through the rotational shaft.

4. A mobile device according to claim 3, further comprising an X-ray tube attached to the holding section so that the X-ray tube is moved vertically along the hollow column.

5. A mobile device according to claim 4, wherein said holding section is formed of a carriage attached to the hollow column and a side arm attached to the carriage, said side arm being disposed perpendicularly to the hollow column and holding the X-ray tube at one end thereof.

6. A mobile device according to claim 1, wherein said hollow column and the rotational shaft are integrally formed together as one unit.

7. A mobile device according to claim 1, wherein said lower part of the counter weight has a diameter smaller than that of an upper part of the counter weight and projecting downwardly from the upper part, said diameter being substantially same as an inner diameter of the hollow part of the rotational shaft.

* * * * *